United States Patent [19]

Limbert et al.

[11] Patent Number: 4,701,452
[45] Date of Patent: Oct. 20, 1987

[54] USE OF CEPHEM COMPOUNDS AS IMMUNOMODULATORS

[75] Inventors: Michael Limbert, Hofheim am Taunus; Walter Dürckheimer, Hattersheim am Main; Hans-Ulrich Schorlemmer, Weimar; Gerhard Dickneite, Marburg, all of Fed. Rep. of Germany

[73] Assignee: Hoechst Aktiengesellschaft, Fed. Rep. of Germany

[21] Appl. No.: 702,319

[22] Filed: Feb. 15, 1985

[30] Foreign Application Priority Data

Feb. 17, 1984 [DE] Fed. Rep. of Germany ....... 3405728

[51] Int. Cl.$^4$ .......................................... A61K 31/545
[52] U.S. Cl. .................................................... 514/206
[58] Field of Search .......................................... 514/206

[56] References Cited

U.S. PATENT DOCUMENTS 4,454,129  6/1984  Mencke et al. ..................... 514/206

OTHER PUBLICATIONS

European Patent Application No. 0 064 256, (title page).
European Patent Application No. 0 078 532, (title page).
Schleupner & Glasgow, Infection and Immunity, 21: 886–845, (1978).
Watanabe et al., J. Antibiotics, 38: 1781–1787, (1985).
Mayer & Drews, Infection, 8: 13–21, (1980).

*Primary Examiner*—Jerome D. Goldberg
*Attorney, Agent, or Firm*—Finnegan, Henderson, Farabow, Garrett & Dunner

[57] ABSTRACT

The use of cephem compounds of the general formula I

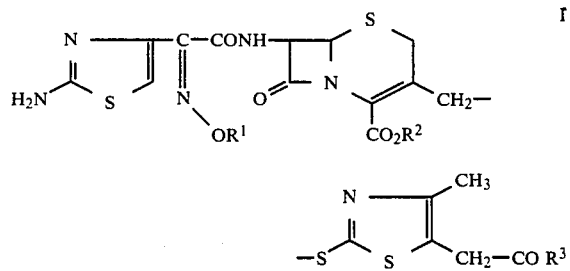

to increase the immunological responsiveness of mammals and formulations which contain an effective content of cephem compounds of the general formula I.

2 Claims, No Drawings

USE OF CEPHEM COMPOUNDS AS IMMUNOMODULATORS

The invention relates to the use of cephem compounds of the general formula I

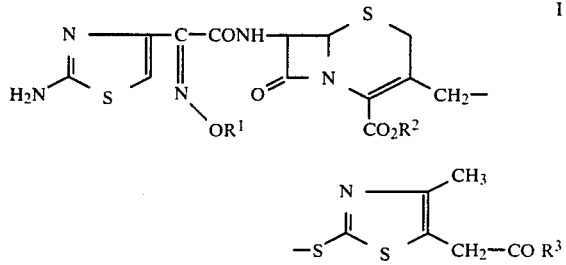

in which the substituents $R^1$, $R^2$ and $R^3$ have the following meanings $R^1$ = hydrogen, optionally substituted alkyl, carboxymethyl, in which the carboxyl group can also be in the form of a physiologically acceptable salt or physiologically acceptable ester, alkoxycarbonylmethyl, aminocarbonylmethyl or cyanomethyl, it also being possible for the methylene group in these radicals optionally to be substituted, $R^2$ = hydrogen, a physiologically acceptable cation or a physiologically acceptable ester group, $R^3$ = hydroxyl, optionally substituted alkoxy, optionally substituted alkenoxy, alkynoxy, cycloalkoxy, optionally substituted aryloxy, optionally substituted aralkoxy, amino, alkylamino, dialkylamino, it also being possible for the two alkyl groups to be closed to form a 4- to 7-membered ring which optionally also contains another nitrogen or an oxygen atom, alkenylamino, optionally substituted arylamino or aryl-$CH_2$-amino, and in which the $R^1O$ group is in the syn-position, for the modulation of the immune system of humans and animals.

The substituents $R^1$, $R^2$ and $R^3$ can have, for example, the following meaning.

If $R^1$ represents optionally substituted alkyl, then one which is especially suitable has 1 to 4 carbon atoms, preferably methyl, ethyl, n-propyl, iso-propyl, n-butyl and iso-butyl, particularly preferably methyl, it being possible for these alkyl groups to be substituted once or several times, preferably once, by, in particular, halogen, preferably chlorine and bromine, hydroxyl or sulfo. Examples of preferred substituted alkyl radicals which may be mentioned are 2-chloroethyl and 2-bromoethyl.

If $R^1$ denotes optionally substituted alkoxycarbonylmethyl, then again in this case a preferred group contains 1 to 4 carbon atoms in the alkyl moiety, in particular methoxycarbonylmethyl and ethoxycarbonylmethyl.

$R^1$ in the meaning of carboxymethyl, which can also be in the form of its physiologically acceptable salts and esters, alkoxycarbonylmethyl, aminocarbonylmethyl and cyanomethyl can also be substituted once or twice in the methylene group, for example by alkyl having 1 to 4 carbon atoms, preferably methyl, it also being possible for 2 alkyl substituents to be closed to form, in particular, a 3- to 6-membered, preferably 5- to 6-membered, carbocyclic ring. Groups which are preferred for this definition and which may be mentioned are carboxymethyl, 1-carboxyethyl, 2-carboxyethyl, 2-carboxyisopropyl, methoxycarbonylmethyl, ethoxycarbonylmethyl, aminocarbonylmethyl and cyanomethyl.

Compounds in which $R^1$ represents hydrogen are also to be regarded as preferred.

If $R^2$ represents a physiologically tolerated ester group, then suitable examples are 1-acyloxyalkyl having 1 to 6, preferably 1 to 4, carbon atoms in both the acyl and the alkyl moiety, such as, for example, acetoxymethyl, 1-acetoxyethyl, 1-acetoxypropyl, 1-acetoxyisopropyl, 1-acetoxyhexyl, propionyloxymethyl, 1-propionyloxyethyl, 1-propionyloxypropyl, 1-propionyloxyhexyl, 1-pivaloyloxymethyl and 1-pivaloyloxyethyl, but in particular acetoxymethyl, 1-acetoxyethyl, 1-propionyloxyethyl and pivaloyloxymethyl.

Particularly preferred for $R^2$ are ester groups which can be eliminated under physiological conditions, such as, for example,

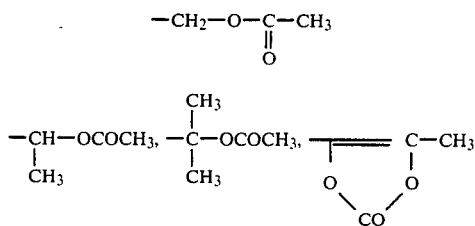

Examples of physiologically acceptable cations which may be mentioned for $R^2$ are alkali metal ions, in particular the sodium and potassium ion, alkaline earth metal ions, in particular the calcium and magnesium ion, and an ammonium ion, but preferably a sodium ion, an optionally substituted alkylated ammonium ion, it being possible for one alkyl radical to have 1 to 4 carbon atoms, such as, in particular, triethylammonium, diethylammonium, dimethylammonium or morpholinium, as well as basic aminoacids, such as, for example, lysine or arginine in their protonated form.

The same physiologically acceptable cations and esters are also suitable for the case when $R^1$ is in the form of a salt or ester of the carboxyalkyl group.

$R^3$ can, for example, represent hydroxyl, alkoxy having 1 to 6, preferably 1 to 4, carbon atoms, which can be substituted once or several times, preferably once, by hydroxyl, halogen, preferably chlorine and bromine, carboxyl, aminocarbonyl, alkoxy having 1 to 4 carbon atoms, alkoxyalkoxy having 1 to 4 carbon atoms per alkyl moiety, alkoxyalkoxyalkoxy having 1 to 4 carbon atoms per alkyl moiety, aryl or aryloxy, in particular phenyl or phenyloxy, it also being possible for aryl optionally to be substituted once or several times, preferably once, by hydroxyl, alkyl having 1 to 4 carbon atoms, alkoxy having 1 to 4 carbon atoms, halogen, in particular chlorine and bromine, carboxyl, alkoxycarbonyl having 1 to 4 carbon atoms in the alkyl moiety or aminocarbonyl, represent alkenoxy having 2 to 6, preferably 2 to 3, carbon atoms, which can be substituted once or several times, preferably once, by phenyl, which in turn can also be substituted once or several times, preferably once, by hydroxyl, alkyl having 1 to 4 carbon atoms, alkoxy having 1 to 4 carbon atoms, halogen, preferably chlorine and bromine, carboxyl, alkoxycarbonyl having 1 to 4 carbon atoms in the alkyl moiety or aminocarbonyl, represent alkynoxy having 2 to 6, preferably 2 to 3, carbon atoms, represent cycloalkoxy having 3 to 6, preferably 5 to 6, carbon atoms, represent aryloxy, preferably phenyloxy, which can optionally also be substituted once or several times, preferably once or twice, by halogen, in particular chlorine and bromine, alkyl having 1 to 4 carbon atoms, hydroxyl, alkoxy having 1 to 4 carbon atoms, nitro, amino, alkylamino having 1 to 4 carbon atoms, dialkylamino having 1 to 4 carbon atoms per alkyl moiety, sulfo, aminocarbonyl, carboxyl or alkoxycarbonyl having 1 to 4 carbon atoms in the alkyl moiety, represent aralkoxy, preferably phenylalkoxy having 1 to 6, preferably 1 to 2, carbon atoms in the alkyl moiety, it also being possible for the aryl moiety optionally to be substituted once or several times, preferably once or twice, by halogen, preferably chlorine and bromine, alkyl having 1 to 4 carbon atoms, hydroxyl, alkoxy having 1 to 4 carbon atoms, nitro, amino, alkylamino having 1 to 4 carbon atoms, dialkylamino having 1 to 4 carbon atoms per alkyl moiety, sulfo, carboxyl, alkoxycarbonyl having 1 to 4 carbon atoms in the alkyl moiety or aminocarbonyl, represent amino, represent alkylamino having 1 to 4 carbon atoms in the alkyl moiety, represent dialkylamino having 1 to 4 carbon atoms per alkyl moiety, it also being possible for the alkyl moieties to be closed to form a 4- to 7-membered, preferably 5- to 6-membered, ring which optionally also contains another nitrogen atom or an oxygen atom, represent alkenylamino having 2 to 4, preferably 2 to 3, carbon atoms in the alkenyl moiety, or represent arylamino or arylmethylamino, in particular phenylamino or benzylamino, it also being possible for the aryl moiety optionally to be substituted once or several times, preferably once, by halogen, in particular chlorine or bromine, alkyl having 1 to 4 carbon atoms, hydroxyl, alkoxy having 1 to 4 carbon atoms, nitro, amino, alkylamino having 1 to 4 carbon atoms, dialkylamino having 1 to 4 carbon atoms per alkyl moiety, sulfo, carboxyl, alkoxycarbonyl having 1 to 4 carbon atoms in the alkyl moiety or aminocarbonyl.

Some groups which are of particular interest according to the invention for $R^3$ may be listed below.

If $R^3$ represents optionally substituted alkoxy having 1 to 6 carbon atoms, then methoxy, ethoxy, propoxy, iso-propoxy, butoxy, iso-butoxy, tert.-butoxy, methoxyethoxy, ethoxyethoxy, methoxyethoxyethoxy, methoxyethoxyethoxyethoxy, ethoxyethoxyethoxyethoxy, phenoxyethoxy, 4-chlorophenoxyethoxy, 4-methylphenoxyethoxy and 4-methoxyphenoxyethoxy may be particularly mentioned, methoxy, ethoxy, iso-propoxy, iso-butoxy, tert.-butoxy, methoxyethoxy, methoxyethoxyethoxy, phenoxyethoxy and 4-chlorophenoxyethoxy being particularly preferred.

If $R^3$ represents optionally substituted alkenoxy then allyloxy and cinnamyloxy may be mentioned as particularly preferred.

Propargyloxy is particularly preferred for $R^3$ in the meaning of alkynoxy.

$R^3$ in the meaning of cycloalkoxy can be, for example, cyclopropoxy, cyclobutoxy, cyclopentyloxy or cyclohexyloxy, but in particular cyclopentyloxy and cyclohexyloxy.

If $R^3$ represents aryloxy, then phenoxy, 4-tolyloxy, 2-chloro and 4-chlorophenoxy, 3,4-dichlorophenoxy, 2-hydroxy and 4-hydroxyphenoxy, 3,4-dihydroxyphenoxy, 4-methoxyphenoxy, 3,4-dimethoxyphenoxy, 4-nitrophenoxy, 2-nitrophenoxy, 4-aminophenoxy, 4-dimethylaminophenoxy, 4-diethylaminophenoxy, 4-sulfophenoxy, 4-carboxyphenoxy, 2-carboxyphenoxy, 4-ethoxycarbonylphenoxy and 4-aminocarbonylphenoxy may be particularly mentioned, phenoxy, 4-chlorophenoxy, 3,4-dichlorophenoxy, 4-methoxyphenoxy, 3,4-dimethoxyphenoxy and 4-dimethylaminophenoxy being particularly preferred.

$R^3$ in the meaning of aralkoxy can represent, for example, benzyloxy, 4-methylbenzyloxy, 4-chlorobenzyloxy, 4-methoxybenzyloxy, 3,4-dimethoxybenzyloxy, 4-hydroxybenzyloxy, 4-nitrobenzyloxy, 4-carboxybenzyloxy, 2-carboxybenzyloxy, 4-ethoxycarbonylbenzyloxy, 4-aminocarbonylbenzyloxy, 4-dimethylaminobenzyloxy and phenethoxy, but preferably represents benzyloxy, 4-chlorobenzyloxy, 3,4-dichlorobenzyloxy, 4-methoxybenzyloxy, 3,4-dimethoxybenzyloxy, 4-carboxybenzyloxy, 4-aminobenzyloxy and 4-dimethylaminobenzyloxy.

$R^3$ in the meaning of alkylamino can represent, for example, methylamino, ethylamino, propylamino or butylamino, but preferably represents methylamino and ethylamino.

If $R^3$ represents dialkylamino, then examples which may be mentioned are dimethylamino, diethylamino, dipropylamino, diisopropylamino, 1-piperidyl, 1-pyrrolidinyl, 1-piperazinyl, 4-ethyl-1-piperazinyl, and 4-morpholinyl, but preferably dimethylamino, diethylamino, 1-piperidyl, 1-pyrrolidinyl and 4-morpholinyl.

If $R^3$ represents alkenylamino, then allylamino may be particularly mentioned.

$R^3$ in the meaning of arylamino can represent, for example, anilino, 4-tolylamino, 4-chlorophenylamino, 4-hydroxyphenylamino, 4-methoxyphenylamino, 2-methoxyphenylamino, 4-nitrophenylamino, 4-aminophenylamino, 4-methylaminophenylamino, 4-dimethylaminophenylamino, 4-sulfophenylamino, 4-carboxyphenylamino, 2-carboxyphenylamino, 4-ethoxycarbonylphenylamino and 4-aminocarbonylphenylamino, but preferably represents anilino, 4-chlorophenylamino, 4-methoxyphenylamino, 4-carboxyphenylamino and 4-aminocarbonylphenylamino. Corresponding substitutions are also suitable for the aryl-$CH_2$-amino group.

Particularly preferred for the use according to the invention is cefodizim (HR 221) which corresponds to a compound of the general formula I in which $R_1 = CH_3$, $R_2$ denotes Na and $R_3$ denotes ONa.

Compounds of the general formula I and their preparation are described, for example, in German Offenlegungsschriften Nos. 2,716,707, 3,117,438 and 3,143,537.

It is known that the living organism has humoral and cellular immunological defense mechanisms. They serve to neutralize and to eliminate foreign bodies which have penetrated and which may induce pathogenetic changes. There are many disorders which are accompanied by impairment of the immune system or in which its function is insufficient to deal with the pathogens, such as, for example, microorganisms. For this reason, people have long sought immunomodulating substances which, because of their high efficacy and good tolerability, allow wide use to support the defenses of the body.

The present invention describes a new class of substances which have immunopharmacological activity, are chemically defined, have low toxicity and, moreover, are outstanding antibiotics for controlling local and systemic bacterial infections. It is known that many compounds which have good antibiotic activity, such as, for example, chloramphenicol or tetracycline, may have an adverse effect on the defenses of the body. Thus, it was surprising that the compounds according to the invention have, at low concentration, an advantageous effect on the immune response, that is to say they lead to an increase in the immunological responsiveness without showing toxic side effects.

Hence, the new compounds are suitable not only as broad-spectrum antibiotics but also display a second main action due to their immunostimulating properties. This can be of great importance for the successful recovery of patients who have lowered resistance which is acquired or inborn. Furthermore, the new compounds can also be used to protect from infections or to accelerate the elimination of microorganisms or degenerate cells from the body. For example, it is possible in animal experiments to have such a favorable effect on candida infection of mice, which has a fatal course, by prophylactic administration of cefodizim for the survival rate to be $\geq 65\%$ at the end of the observation period (14 days). In the same observation period, not one animal in the control group survives.

According to the invention, the active compounds can be administered both parenterally and orally.

The amount which has an immunomodulating effect is in the range 1-200, preferably 10-50, mg per kg of body weight on parenteral administration. The active compound can be administered alone or combined with other medicaments which have favorable effects on infections and carcinoses. Solutions or suspensions of the active compound are suitable for oral and parenteral administration. For the preparation of aqueous solutions, the active compound is preferably used in the form of salts which are soluble in water and physiologically tolerated, as are evident from, for example, the definitions of $R^2$ listed above. The formulations can contain customary auxiliaries and vehicles. Suitable examples of these are fillers, emulsifiers, lubricants and buffers. The active compound is mixed as the free acid or as a salt with the pharmaceutical auxiliaries. If the free acid is selected, then the equivalent amount of an appropriate base should be added to the auxiliaries. When the active compound is used in the form of suspensions, preferred suitable pharmaceutically tolerated vectors are hydroxyl-free solvents, such as, for example, vegetable oils.

The experimental results which follow are examples of the immunomodulating action of the compounds of the general formula I. A variety of test methods which are known to be suitable for assessing this type of effect were used.

EXAMPLE 1

Stimulation of mouse peritoneal macrophages

Macrophages play a central part in the resistance to infections and in the immune response. On the one hand, they are themselves involved in the elimination of pathogens, and on the other hand they have control functions in the regulation of the humoral (B-cell-dependent) and the cellular (T-cell-dependent) immune response.

Cefodizim was administered 1× intravenously, in various concentrations between 7.5 and 60 mg/kg mouse, to NMRI mice. 72 h after administration of the product, the peritoneal macrophages were isolated and tested for various functions. Compared with macrophages from the control group, the chemiluminescence reaction of the macrophages from animals treated with cefodizim (15-60 mg/kg mouse) was significantly increased as a function of the dose (Table 1).

The macrophages from the mice treated with cefodizim (formula I, $R^1=CH_3$, $R^2=Na$, $R^3=ONa$) were also distinguished by an increased content of lysosomal enzymes (Table 1).

The pinocytosis of colloidal gold ($^{198}Au$) by macrophages from animals treated with cefodizim was significantly increased compared with the macrophages from untreated animals ($0.207 \times 10^3$ cpm control vs. $0.43 \times 10^3$ for the macrophages from animals treated with cefodizim).

TABLE 1

| Cefodizim dose i.v. (mg/kg mouse) 1 × 72 h before test | Chemiluminescence reaction (RLU/15 min) | Content of lysosomal enzymes (mU/ml) |
|---|---|---|
| 0 (Control) | $1.63 \times 10^5$ | $0.9 \times 10^3$ |
| 7.5 | $2.73 \times 10^5$ | $1.2 \times 10^3$ |
| 15 | $4.13 \times 10^5$ | $1.6 \times 10^3$ |
| 30 | $5.92 \times 10^5$ | $1.8 \times 10^3$ |
| 60 | $7.80 \times 10^5$ | $2.0 \times 10^3$ |

EXAMPLE 2

Potentiation of the immunological response of the delayed type (delayed-type hypersensitivity, DTH)

This test provides information on the functioning of the T-cell-dependent component of the immune system. NMRI mice were pretreated several times with various intraperitoneal doses of cefodizim. On the last day the product was administered, all the animals were immunized i.v. with erythrocytes from sheep's blood. The DTH response to an intraplantar injection of erythrocytes from sheep's blood was measured after a further 5 days.

It emerges that the animals which have been pretreated with cefodizim have a more pronounced DTH response than do corresponding control animals (Table 2).

TABLE 2

| Cefodizim dose i.p. (mg/kg) 2 × daily for 4 days | DTH response to erythrocytes from sheep's blood increase in paw swelling (%) |
|---|---|
| 0 (Control) | 21.6 |
| 30 | 26.9 |
| 40 | 30.5 |

The result of this experiment shows that prophylactic administration of cefodizim has a stimulating effect on the T-cell-system of the mouse.

EXAMPLE 3

Increase in the resistance of Balb/c mice to a *Candida albicans* infection

Balb/c mice receive intraperitoneal administration of cefodizim doses of 2×30 mg/kg/day for 4 days. 24 h after the last administration of cefodizim, these animals and the control animals, who had received administration of physiological saline solution in the same volumes and time intervals, are infected intravenously with *Candida albicans* ($5 \times 10^6$ CFU/mouse). The animals in the control group die after a mean of 3.5 days, and all animals have died after 6 days at the most. After an observation period of 14 days, ≧65% of the group treated with cefodizim survive. The result of this infection experiment indicates that the resistance of the Balb/c mice to infection by *Candida albicans* was increased following prophylactic administration of cefodizim.

EXAMPLE 4

Stimulation of the DTH response and the macrophage activity by various derivatives of cefodizim As already described in Examples 1 and 2, NMRI mice were treated parenterally with various concentrations (10-200 mg/kg) of cefodizim and, for comparison, with compounds of the general formula I in which the substituents have the following meanings:

| Compound | $R_1$ | $R_2$ | $R_3$ |
|---|---|---|---|
| A | —CH$_3$ | H | —OCH$_2$—⟨phenyl⟩—OCH$_3$ |
| B | —CH$_3$ | H | —OCH$_2$—⟨phenyl(OCH$_3$)⟩—OCH$_3$ |
| C | —CH$_3$ | H | —OCH$_2$—⟨phenyl⟩—Cl |
| D | —CH$_3$ | H | —OC$_2$H$_4$—⟨phenyl⟩ |
| E | —CH$_3$ | H | —NH$_2$ |

The macrophage function (chemiluminescence and enzyme activity) and DTH response were investigated as tests to detect the immunostimulation.

Table 3 below shows the relative efficacy of the individual substances related to cefodizim. The 100% figure corresponds to the maximum activation (difference between control and stimulation) by cefodizim, as indicated to Tables 1 and 2.

TABLE 3

| Compound (10-200 mg/kg) | Macrophage activity | | DTH response (SRBC) |
|---|---|---|---|
| | Chemiluminescence | Exocytosis | |
| Cefodizim | 100% | 100% | 100% |
| A | 121% | 113% | 116% |
| B | 37% | 62% | 84% |
| C | 50% | 84% | 87% |
| D | 178% | 149% | 112% |
| E | 43% | 68% | 0% |

It can be seen from the table that, compared with macrophages from untreated animals, the chemiluminescence reaction of these cells was greatly stimulated and their content of lysosomal enzymes was markedly increased by all the derivatives mentioned, as already shown for cefodizim. In addition, the DTH response of the animals pretreated with cefodizim derivatives was markedly more pronounced than in the corresponding control animals.

We claim:

1. A method of treatment to increase the immunological responsiveness of a mammal which comprises administering to a mammal in need of said treatment an effective amount for said treatment of a compound of the formula

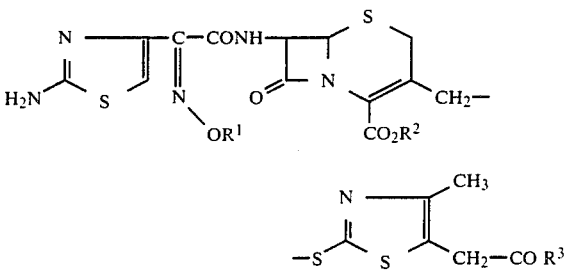

wherein

R$^1$ is hydrogen, or wherein

R$^1$ is alkyl with 1 to 4 carbon atoms or said alkyl substituted by halogen, hydrogen or sulfo, or wherein R$^1$ is carboxymethyl or said carboxymethyl in the form of a physiologically acceptable salt or physiologically acceptable ester, or wherein R$^1$ is aminocarbonylmethyl or cyanomethyl, or wherein R$^1$ is carboxymethyl, carboxymethyl in the form of a physiologically acceptable salt or physiologically acceptable ester, aminocarbonylmethyl or cyanomethyl, each substituted once or twice in the methylene group by alkyl with 1 to 4 carbon atoms or having 2 alkyl substituents closed to form a 3- to 6-membered carbocyclic ring, R$^2$ is hydrogen, or wherein R$^2$ is a physiologically acceptable cation, or wherein R$^3$ is a hydroxyl, or wherein R$^3$ is alkoxy with 1 to 6 carbon atoms or said alkoxy mono- or polysubstituted by hydroxyl, halogen, carboxyl, aminocarbonyl, alkoxy with 1 to 4 carbon atoms, alkoxyalkoxy with 1 to 4 carbon atoms per alkyl moiety, alkoxyalkoxyalkoxy with 1 to 4 carbon atoms per alkyl moiety, alkyl with 1 to 4 carbon atoms, halogen, carboxyl, alkoxycarbonyl with 1 to 4 carbon atoms in the alkyl moiety or aminocarbonyl, or wherein R$^3$ is alkenoxy with 2 to 6 carbon atoms or said alkenoxy mono- or polysubstituted by phenyl or said phenyl mono- or polysubstituted by alkyl with 1 to 4 carbon atoms, alkoxy with 1 to 4 carbon atoms, halogen, carboxyl, alkoxycarbonyl with 1 to 4 carbon atoms in the alkyl moiety or aminocarbonyl, or wherein R$^3$ is alkynoxy with 2 to 6 carbon atoms, or wherein R$^3$ is cycloalkoxy with 3 to 6 carbon atoms, or wherein R$^3$ is benzyloxy which may be substituted by halogen, alkyl with 1 to 4 carbon atoms, hydroxyl, alkoxy with 1 to 4 carbon atoms, nitro, amino, alkylamino with 1 to 4 carbon atoms, dialkylamino with 1 to 4 carbon atoms per alkyl moiety, sulfo, aminocarbonyl, carboxyl or alkoxycarbonyl with 1 to 4 carbon atoms in the alkyl moiety, or wherein $R^3$ is aralkoxy with 1 to 6 carbon atoms in the alkyl moiety or said aralkoxy wherein the aryl moiety is mono- or polysubstituted by halogen, alkyl with 1 to 4 carbon atoms, hydroxyl, alkoxy with 1 to 4 carbon atoms, nitro, amino, alkylamino with 1 to 4 carbon atoms, dialkylamino with 1 to 4 carbon atoms per alkyl moiety, sulfo, carboxyl, alkoxycarbonyl with 1 to 4 carbon atoms in the alkyl moiety or aminocarbonyl, or wherein $R^3$ is amino, or wherein $R^3$ is alkylamino with 1 to 4 carbon atoms in the alkyl moiety, or wherein $R^3$ is dialkylamino with 1 to 4 carbon atoms per alkyl moiety or said dialkylamino with the alkyl moieties closed to form a 4- to 7-members ring or said ring containing another nitrogen atom or an oxygen atom, or wherein $R^3$ is alkenylamino with 2 to 4 carbon atoms in the alkyl moiety and in which the $R^1O$ group is in the syn-position.

2. A method of treatment to increase the immunological responsiveness of a mammal which comprises administering to a mammal in need of said treatment a formulation comprising an effective amount of a compound of the formula

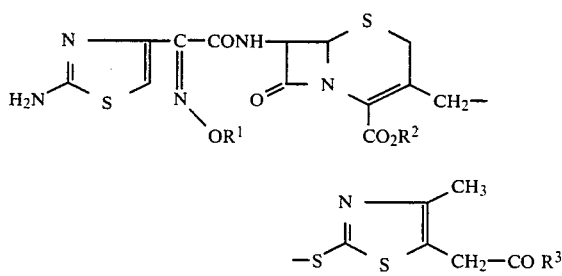

wherein $R^1$ is hydrogen, or wherein $R^1$ is alkyl with 1 to 4 carbon atoms or said alkyl substituted by halogen, hydrogen or sulfo, or wherein $R^1$ is carboxymethyl or said carboxymethyl in the form of a physiologically acceptable acid or physiologically acceptable ester, or wherein $R^1$ is aminocarbonylmethyl or cyanomethyl, or wherein $R^1$ is carboxymethyl, carboxymethyl in the form of a physiologically acceptable salt or physiologically acceptable ester, aminocarbonylmethyl or cyanomethyl, each substituted once or twice in the methylene group by alkyl with 1 to 4 carbon atoms or having 2 alkyl substituents closed to form a 3- to 6-membered carbocyclic ring, $R^2$ is hydrogen, or wherein $R^2$ is a physiologically acceptale cation, or wherein $R^3$ is a hydroxyl, or wherein $R^3$ is alkoxy with 1 to 6 carbon atoms or said alkoxy mono- or polysubstituted by hydroxyl, halogen, carboxyl, aminocarbonyl, alkoxy with 1 to 4 carbon atoms, alkoxyalkoxy with 1 to 4 carbon atoms per alkyl moiety, alkoxyalkoxyalkoxy with 1 to 4 carbon atoms per alkyl moiety, alkyl with 1 to 4 carbon atoms, halogen, carboxyl, alkoxycarbonyl with 1 to 4 carbon atoms in the alkyl moiety or aminocarbonyl, or wherein $R^3$ is alkenoxy with 2 to 6 carbon atoms or said alkenoxy mono- or polysubstituted by phenyl or said phenyl mono- or polysubstituted by alkyl with 1 to 4 carbon atoms, alkoxy with 1 to 4 carbon atoms, halogen, carboxyl, alkoxycarbonyl with 1 to 4 carbon atoms in the alkyl moiety or aminocarbonyl, or wherein $R^3$ is alkynoxy with 2 to 6 carbon atoms, or wherein $R^3$ is cycloalkoxy with 3 to 6 carbon atoms, or wherein $R^3$ is benzyloxy which may be substituted by halogen, alkyl with 1 to 4 carbon atoms, hydroxyl, alkoxy with 1 to 4 carbon atoms, nitro, amino, alkylamino with 1 to 4 carbon atoms, dialkylamino with 1 to 4 carbon atoms per alkyl moiety, sulfo, aminocarbonyl, carboxyl or alkoxycarbonyl with 1 to 4 carbon atoms in the alkyl moiety, or wherein $R^3$ is aralkoxy with 1 to 6 carbon atoms in the alkyl moiety or said aralkoxy wherein the aryl moiety is mono- or polysubstituted by halogen, alkyl with 1 to 4 carbon atoms, hydroxyl, alkoxy with 1 to 4 carbon atoms, nitro, amino, alkylamino with 1 to 4 carbon atoms, dialkylamino with 1 to 4 carbon atoms per alkyl moiety, sulfo, carboxyl, alkoxycarbonyl with 1 to 4 carbon atoms in the alkyl moiety or aminocarbonyl, or wherein $R^3$ is amino, or wherein $R^3$ is alkylamino with 1 to 4 carbon atoms in the alkyl moiety, or wherein $R^3$ is dialkylamino with 1 to 4 carbon atoms per alkyl moiety or said dialkylamino with the alkyl moieties closed to form a 4- to 7-members ring or said ring containing another nitrogen atom or an oxygen atom, or wherein $R^3$ is alkenylamino with 2 to 4 carbon atoms in the alkyl moiety and in which the $R^1O$ group is in the syn-position, for increasing the immunological responsiveness of said mammal and a pharmaceutically acceptable carrier of said compound.

* * * * *